US009849598B2

(12) United States Patent
Damkat et al.

(10) Patent No.: US 9,849,598 B2
(45) Date of Patent: Dec. 26, 2017

(54) HAIR CUTTING DEVICE

(71) Applicant: KONINKLIJKE PHILIPS N.V., Eindhoven (NL)

(72) Inventors: Chris Damkat, Eindhoven (NL); Natalia Eduardauna Uzunbajakava, Eindhoven (NL); Calina Ciuhu, Eindhoven (NL); Geert Veenstra, Boornbergum (NL); Harmen Kooiker, Groningen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 496 days.

(21) Appl. No.: 14/364,963

(22) PCT Filed: Dec. 18, 2012

(86) PCT No.: PCT/IB2012/057422

§ 371 (c)(1),
(2) Date: Jun. 12, 2014

(87) PCT Pub. No.: WO2013/093772

PCT Pub. Date: Jun. 27, 2013

(65) Prior Publication Data

US 2014/0345142 A1 Nov. 27, 2014

Related U.S. Application Data

(60) Provisional application No. 61/578,910, filed on Dec. 22, 2011.

(51) Int. Cl.

| | |
|---|---|
| ***A61B 18/20*** | (2006.01) |
| ***B26B 21/40*** | (2006.01) |
| ***B26B 19/38*** | (2006.01) |

(52) U.S. Cl.
CPC .......... *B26B 21/405* (2013.01); *B26B 19/388* (2013.01); *B26B 21/4056* (2013.01)

(58) Field of Classification Search
CPC .................. A61B 18/20; A61B 18/203; A61B 2018/00476; A61B 2018/00636;
(Continued)

(56) References Cited

U.S. PATENT DOCUMENTS 5,182,857 A * 2/1993 Simon .................. A61B 18/203 132/118
5,606,798 A * 3/1997 Kelman ............... A61B 18/203 219/223

(Continued)

FOREIGN PATENT DOCUMENTS

WO 9216338 A1 10/1992
WO 2007117580 A2 10/2007

(Continued)

*Primary Examiner* — Ahmed Farah

(57) ABSTRACT

A hair cutting device (10) is provided comprising a cutter unit (11), a skin stretcher (12) and slit adapting means. The cutter unit (11) comprises a skin-contact surface for dragging over a skin surface (21) in a shaving direction (55), a front surface arranged in front of the skin-contact surface in the shaving direction (55), and a laser beam exit window arranged in the front surface for allowing a hair cutting laser beam (13) to cut a hair (22) near the skin surface (21) in front of the front surface. The skin stretcher (12) is positioned in front of the cutter unit (11), according to the shaving direction (55), and comprises a stretcher surface for dragging over the skin surface (21) together with the skin-contact surface, such that a skin dome (23) is formed by the skin surface (21) in a slit between the skin stretcher (12) and the cutter unit (11). The slit adapting means are provided for adapting at least one dimension (51, 52, 54) of the slit for controlling a shape of the skin dome (23).

13 Claims, 3 Drawing Sheets

(58) Field of Classification Search
CPC A61B 2018/00642; A61B 2018/00648; A61B 2018/0452; A61B 2018/20361; A61B 2018/002255; B26B 19/38; B26B 19/388; B26B 19/3893; B26B 21/4056
USPC ..................... 606/9–12; 607/88–91; 128/898
See application file for complete search history.

(56) References Cited

U.S. PATENT DOCUMENTS

| | | | | |
|---|---|---|---|---|
| 5,993,440 | A | 11/1999 | Ghassemi | |
| 7,197,825 | B2 | 4/2007 | Walker et al. | |
| 9,295,518 | B2 * | 3/2016 | Verhagen | A61B 18/20 |
| 2005/0216035 | A1 | 9/2005 | Kraus et al. | |
| 2009/0049695 | A1 | 2/2009 | Keene et al. | |
| 2011/0197726 | A1 | 8/2011 | Kraus | |
| 2013/0144280 | A1 * | 6/2013 | Eckhouse | A45D 26/00 606/9 |
| 2015/0202006 | A1 * | 7/2015 | Johnson | A61B 18/203 606/9 |
| 2016/0016256 | A1 * | 1/2016 | Moeskops | A61B 18/203 606/9 |

FOREIGN PATENT DOCUMENTS

| | | | |
|---|---|---|---|
| WO | 2008041193 | A2 | 4/2008 |
| WO | 2010066966 | A1 | 6/2010 |
| WO | 2010106480 | A1 | 9/2010 |
| WO | 2011010246 | A1 | 1/2011 |

* cited by examiner

HAIR CUTTING DEVICE

CROSS-REFERENCE TO PRIOR APPLICATIONS

This application is the U.S. National Phase application under 35 U.S.C. §371 of International Application No. PCT/IB2012/057422, filed on Dec. 18, 2012, which claims the benefit of U.S. Provisional Patent Application No. 61/578,910, filed on Dec. 22, 2011. These applications are hereby incorporated by reference herein.

FIELD OF THE INVENTION

This invention relates to a hair cutting device comprising cutter unit and a skin stretcher. The cutter unit comprises a skin-contact surface for dragging over a skin surface in a shaving direction, a front surface arranged in front of the skin-contact surface in the shaving direction, and a laser beam exit window arranged in the front surface for allowing a hair cutting laser beam to cut a hair near the skin surface in front of the front surface. The skin stretcher is positioned in front of the cutter unit, according to the shaving direction, and comprises a stretcher surface for dragging over the skin surface together with the skin-contact surface.

BACKGROUND OF THE INVENTION

Such a hair cutting device is, e.g., known from the international patent application published as WO 2011/010246. Said patent application describes a hair cutting device for cutting hair near skin of a human or animal body part. An optical blade, embodying the functionality of the cutter unit, is dragged over the skin surface, while a reflector in the optical blade directs the hair cutting laser beam to the hair. The optical blade has a tapered end with a curved surface for exerting a local pressure on the skin surface and thereby manipulating the skin in an attempt to improve closeness and minimize skin irritation. Closeness is thereby defined as the length of the remaining stubbles after shaving. Irritation is caused by the hair cutting laser irradiating the skin instead of the hair. WO 2011/010246 further discloses the use of a skin stretcher, installed in front of the optical blade, for stretching the skin and making skin doming more predictable. Skin doming is the piling up of an amount of skin before the front surface of the optical blade when dragging the blade surface over the skin surface in the shaving direction. The aim of this skin manipulation is to ensure that the hair cutting light beam remains parallel to and above the skin surface.

One of the disadvantages of this known hair cutting device is that longer hairs may be trapped between the skin stretcher and the skin while the optical blade passes and will therefore be missed by the hair cutting laser beam. In addition, skin properties like flexibility and smoothness may vary from person to person, within persons on different body sites or positions and perhaps also from day to day, resulting in either reduced closeness or increased irritation.

OBJECT OF THE INVENTION

It is therefore an object of the invention to provide a hair cutting device which provides improved closeness and reduced irritation.

SUMMARY OF THE INVENTION

According to a first aspect of the invention, this object is achieved by providing a hair cutting device comprising a cutter unit, a skin stretcher and slit adapting means. The cutter unit comprises a skin-contact surface for dragging over a skin surface in a shaving direction, a front surface arranged in front of the skin-contact surface in the shaving direction, and a laser beam exit window for allowing a hair cutting laser beam to cut a hair near the skin surface in front of the front surface. The skin stretcher is positioned in front of the cutter unit, according to the shaving direction, and comprises a stretcher surface for dragging over the skin surface together with the skin-contact surface, such that a skin dome is formed by the skin surface in a slit between the skin stretcher and the cutter unit. The slit adapting means are provided for adapting at least one dimension of the slit for controlling a shape of the skin dome.

The inventors have realized that the above mentioned problems of the prior art can be avoided by adapting the slit dimensions to obtain an optimum balance between improving closeness and minimizing irritation. For example, when the hairs to be cut are relatively long or the skin surface is relatively smooth and inelastic, larger slits are preferred. Larger slits decrease the chance that a hair is still trapped underneath the stretcher surface when the cutter unit passes. Larger slits also allow more skin to pile up between the skin stretcher and the cutter unit, thereby increasing the skin dome height. So while smooth and inelastic skin surfaces reduce the tendency of skin to pile up, a larger slit may compensate for that effect and increase skin dome height to improve closeness. When the skin properties are such that the skin dome height is larger than usual, a decrease of the slit size reduces the skin dome height and the irritation caused by the hair cutting laser beam hitting the skin.

The inventors have found out that various slit dimension parameters like slit size and exposure are important parameters for manipulating the skin dome shape and height. Slit size is defined as the distance between a rear surface of the skin stretcher and the front surface of the cutter unit. Exposure is defined as the distance between the skin-contact surface and the stretcher surface measured in a direction perpendicular to the shaving direction. By careful tuning the slit size, the exposure or both, the dome shape can be controlled in order to obtain an optimum balance between closeness and irritation.

The slit size and the exposure may both be adapted by either moving the skin stretcher or the cutter unit relative to each other in the hair cutting device. In principle, also moving both parts is an option, but this would require a more complex construction of the device from a mechanical point of view.

Instead of or in addition to adapting the slit size and exposure, also the angle (hereinafter referred to as the cutter angle) between the skin-contact surface and the shaving direction may be adapted. Changing the cutter angle has two effects on the shaving process. A first effect is that the inclined skin-contact surface exerts a different pressure on the skin surface than a flat skin-contact surface would do which may lead to a different dome shape and dome height. A second effect is that, because the light source is rotated together with the cutter unit, the optical base line of the hair cutting laser will also rotate which means that the focus of the hair cutting laser moves away from or towards the skin surface. Both the change of the dome shape and the modification of the optical baseline affect the closeness and the irritation. It is to be noted that the optical baseline may also be modified independent of the cutter unit, e.g. by mechanically rotating or displacing optical elements in the cutter unit.

In an embodiment of the hair cutting device according to the invention, the device may comprise control means for manually setting the appropriate slit dimensions. The user may, e.g., be enabled to select a slit size and/or an exposure from a discrete or continuous range of available settings. Alternatively, the device may offer different settings for short hair and for longer hair. Each setting then corresponds to a different predetermined slit size and/or exposure. Also, different settings for shaving a beard, a head, arms and/or legs may be provided.

Instead of manually setting the slit dimensions, a processor may be provided which is coupled to the slit adapting means for controlling slit dimensions and skin dome height. The processor is preferably also coupled to one or more sensors for measuring parameters that are indicative of the skin dome height. Some examples of such sensors are described below.

The hair cutting device may further comprise a light based hair detector for detecting the hair near the skin surface, a hair cutting laser source for generating the hair cutting laser beam, and a processor coupled to the light based hair detector and to the hair cutting laser source. The processor is arranged to activate the hair cutting laser source in a focal position of the hair cutting laser beam in which the light based hair detector has detected the presence of the hair. Because the device knows the positions of the hairs, the cutting laser can be selectively targeted at the hairs instead of systematically scanning larger areas where hairs may be present. As a result, skin irritation is considerably reduced.

In an embodiment of the hair cutting device according to the invention, the light based hair detector is further adapted to detect a height of the skin dome and the processor is further arranged to control the slit adapting means in dependence of the detected height of the skin dome. The light based hair detector is already equipped to distinguish hairs from skin and may thus also be used for detecting the skin dome height. When the skin dome height is known, it can also be controlled by adapting the slit dimensions. In general, lower skin dome height improves closeness but also increases irritation.

Optionally, the skin stretcher comprises a pressure sensor for determining a pressure exerted on the stretcher surface and wherein the processor is further arranged to control the slit adapting means in dependence of the determined pressure. When a user pushes the hair cutting device into the skin with too much force, the chances of the focal point of the hair cutting laser falling within the skin is considerably increased. To avoid irritation of the skin, the slit dimension may then be adapted in order to reduce skin dome height and thus irritation.

Additionally or alternatively, the skin stretcher comprises a friction sensor for determining a friction between the stretcher surface and the skin surface and wherein the processor is further arranged to control the slit adapting means in dependence of the determined friction. Friction of the skin surface may depend on, e.g., skin type, use of shaving lubricants, hair length and pressure applied by the hair cutting device. More friction leads to a higher skin dome, which can be compensated by appropriate changes to the slit dimensions.

Optionally, also a means for determining a speed of the hair treatment device relative to the skin surface is provided and the processor is further arranged to control the slit adapting means in dependence of the determined speed.

These and other aspects of the invention are apparent from and will be elucidated with reference to the embodiments described hereinafter.

DETAILED DESCRIPTION OF THE INVENTION

Figure 1:
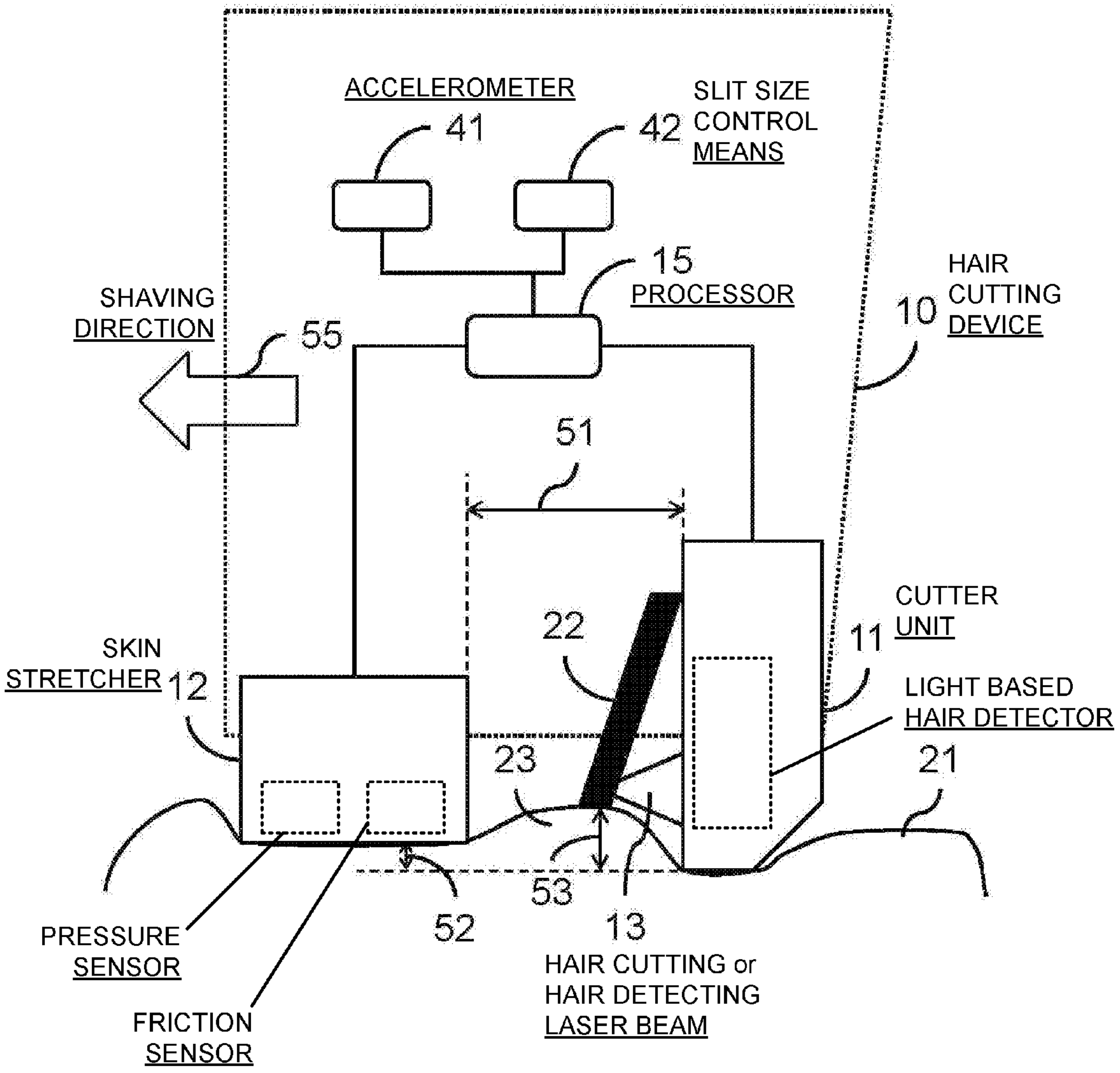
FIG. 1 schematically shows a cross section of a hair cutting device according to the invention, FIG. 2 schematically shows a top view cross section of the hair cutting device of FIG. 1.

FIG. 1 schematically shows a cross section of a hair cutting device 10 according to the invention. The hair cutting device 10 comprises a cutter unit, here in the form of an optical blade 11, optionally with a tapered end as also described in the international patent application published as WO 2011/010246. The optical blade 11 comprises optical elements like mirrors, reflectors and lenses for directing a hair cutting laser beam 13 through an exit window of the optical blade 11 and focusing the hair cutting laser beam 13 in a focal point near the skin surface 21. The optical blade 11 preferably also comprises the light source for the hair cutting laser beam 13. The same or additional optical elements may also be used by a light based hair detector which is used for distinguishing hairs 22 from skin 21. The hair detector and the hair cutting laser may both use the same light source, possibly at a different intensity. Alternatively, separate light sources may be provided for detecting and cutting hairs 22. The light based hair detector and the hair cutting laser are controlled by a processor 15, which is coupled to the light source(s) and the light detector(s) of the light based hair detector. This processor 15 is preferably provided in the body of the hair cutting device 10 and also serves for controlling other parts if the device 10. It is to be noted that the hair cutting device 10 may also function very well without using a hair detector. For example, the hair cutting laser beam 13 may just be focused at a standard height above the skin-contact surface or blade surface and may systematically scan larger areas where hairs 22 may be present.

During shaving, the user moves the hair cutting device 10 over the skin surface 21. The preferred shaving direction 55 is against the grain because this leads to beneficial hair manipulation, e.g. due to additional hair lift, and an improved shaving result. In front of the optical blade 11, a skin stretcher 12 is provided. One of the functions of the skin stretcher 12 is to bring the hairs 22 in a detection area and to achieve hair lift. The detection area is the open space between the optical blade 11 and the skin stretcher 12 where a focused light beam 13 of the hair detector is able to detect the hair 22. The hairs 22 are brought in the detection area by assuring stretching of the skin 21 by the skin stretcher 12 and subsequent contact between the hair 22 and the optical blade 11. Hair lift is achieved due to a shear force, exerted by the skin stretcher 12, and hair rotation around its anchorage point in the skin 21 (due to skin stretching as well as due to hair-optical blade contact).

When dragging the skin stretcher 12 and the optical blade 11 over the skin surface 21, a skin dome 23 is formed in the slit between the stretcher 12 and the blade 11. The skin dome 23 is a small amount of piled up skin 21 in front of the optical blade 11. The height 53 and shape of the skin dome 23 depends on multiple factors, such as the shaving speed, shaving direction, skin smoothness, skin flexibility, use of shaving lubricants, pressure exerted on the skin by the hair cutting device, etc. An important function of the skin stretcher 12 is to reduce the variation in skin dome 23 dimensions. The more constant the skin dome 23 shape and dimensions are, the closer to the skin surface 21 the hair cutting laser beam 13 can be focused without causing too much skin irritation.

According to the invention, the slit dimensions can be adapted for controlling the skin dome 23 shape and height 53. Two important slit dimensions that may be adapted are the slit size 51 and the exposure 52. The slit size 51 is the width of the slit as defined by the distance between a back surface of the skin stretcher 12 and a front surface of the optical blade 11. Exposure 52 is the distance between the stretcher surface of the skin stretcher 12 and the blade surface of the optical blade 11, measured in a direction perpendicular to those surfaces (and the skin surface 21). Skin dome height 53 may, e.g., be increased by increasing the slit size 51 and/or decreasing the exposure 52 or decreased by decreasing the slit size 51 and/or increasing the exposure 52. Changing the slit size 51 and/or exposure 52 may be realized by moving the skin stretcher 12 and/or the optical blade 11 relative to each other in the hair cutting device 10. The slit adapting means may comprise actuators for providing the required movements which are preferably also controlled by the processor 15. In practice, it may be easier to only move the skin stretcher 12 and not the optical blade 11. The optical blade 11 already comprises a lot of mechanical and electronic parts for enabling hair detection and cutting of the hairs 22. Adding mechanical actuators for moving the optical blade 11 may be more complex from a constructional point of view than providing actuators for moving the skin stretcher 12. Suitable parameter ranges for the slit size may, e.g., be about 0.5 and 2.0 mm. The exposure may, e.g., be chosen in the range 0-250 μm (micrometer).

It is to be noted that the skin stretcher 12 and/or the cutter unit 11 may have some additional freedom of movement for following irregularities of the skin or body parts to be shaved. For example, the skin stretcher 12 and/or the cutter unit 11 may be mounted to the hair cutting device 10 with some springs allowing the skin stretcher 12 and/or cutter unit 11 to follow the contours of the body part during shaving. The skin stretcher 12 and the cutter unit 11 may move in union relative to the hair cutting device 10 in order to follow the skin contours. It is, however, important that this additional freedom of movement is not so large that it interferes with the skin dome control process.

In an embodiment of the hair cutting device according to the invention, the hair cutting device 10 may comprise control means for manually setting the appropriate slit dimensions. The user may, e.g., be enabled to select a slit size 51 and/or an exposure 52 from a discrete or continuous range of available settings. For this purpose, control means 42 may be provided at the outer surface of the hair cutting device 10. The control means 42 are coupled to the processor 15 and may also enable controlling other functions of the hair cutting device 10. The control means 42 may, e.g., comprise as an on/off switch for turning the device 10 on or off. Alternatively, the device may offer different settings for short hair and for longer hair. Each setting then corresponds to a different predetermined slit size and/or exposure. Also, different settings for shaving a beard, a head, arms and/or legs may be provided. The user may be allowed to put the skin stretcher 12 or the optical blade 11 in one of the predetermined settings manually or the selected settings may be received by the processor 15 which then controls one or more actuators for moving the appropriate parts of the device 10. Alternatively, the appliance could offer a "test shave" in which the detection sensors are enabled and the cutting laser beam 13 is temporarily disabled. The information is then used to either set or propose an optimal setting.

In preferred embodiments, the processor 15 is arranged to control the skin dome height 53 by adapting slit dimensions in response to measurements of parameters that are indicative of or have an influence on the skin dome height 53. For example, the light based hair detector may be adapted to detect the skin dome height 53. The processor 15 may then be arranged to control the actuators in dependence of the detected skin dome height 53. The light based hair detector is already equipped to distinguish hairs 22 from skin 21. The processor can thus easily be programmed to be able to detect the skin dome height 53. For example, the light based hair detector may be used to determine, at one or more selected heights above the skin-contact surface, whether there is skin tissue 21 present or not. When the skin dome height 53 is known, for example from the detection statistics, it can also be controlled by adapting the slit dimensions accordingly.

Optionally, the skin stretcher 12 comprises a pressure sensor for determining a pressure exerted on the stretcher surface and the processor 15 is further arranged to control the slit adapting means in dependence of the determined pressure. When a user pushes the hair cutting device 10 into the skin 21 with too much force, the chances of the focal point of the hair cutting laser 13 falling within the skin 21 is considerably increased. To avoid irritation of the skin 21, the slit dimension may then be adapted in order to reduce skin dome height 23 and thus irritation.

Additionally or alternatively, the skin stretcher 12 comprises a friction sensor for determining a friction between the stretcher surface and the skin surface 21 and the processor 15 is further arranged to control the slit adapting means in dependence of the determined friction. Friction of the skin surface 21 may depend on, e.g., skin type, use of shaving lubricants, hair length and pressure applied by the hair cutting device 10. More friction leads to a higher skin dome 23, which can be compensated by appropriate changes to the slit dimensions.

Optionally, also a means for determining a speed of the hair treatment device 10 relative to the skin surface 21 is provided and the processor 15 is further arranged to control the slit adapting means in dependence of the determined speed. For example, one or more accelerometers 41 may be used for determining the speed or changes in speed of the hair cutting device 10. The accelerometers 41 are coupled to the processor 15 and may be positioned in any part of the hair cutting device 10.

Figure 2:
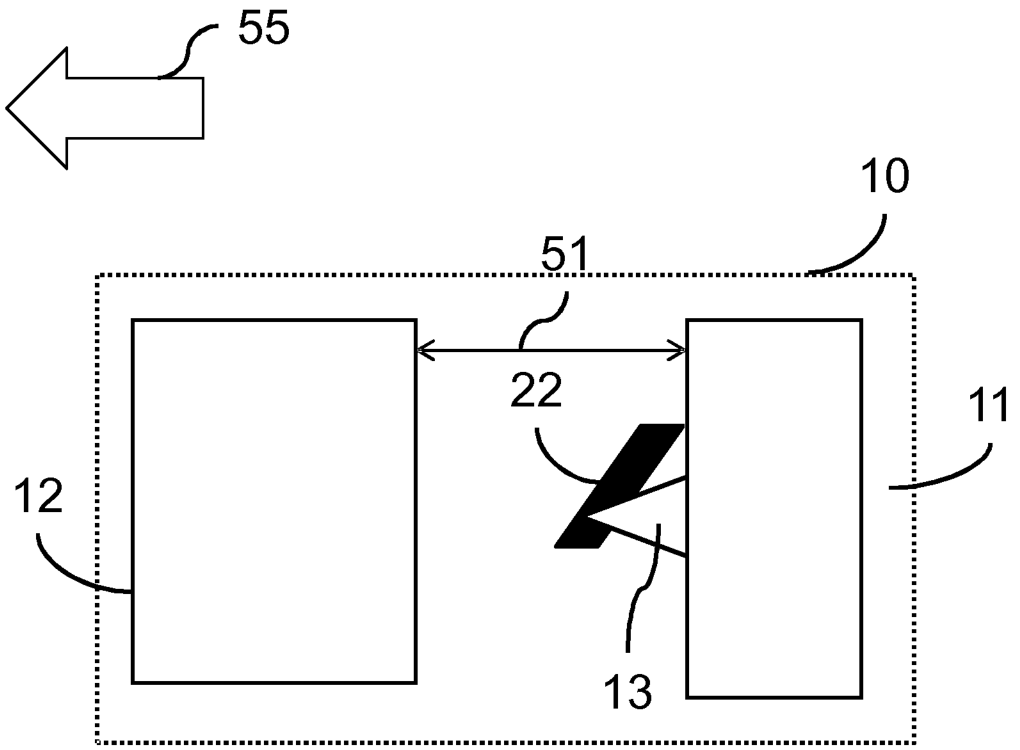
Figure 3:
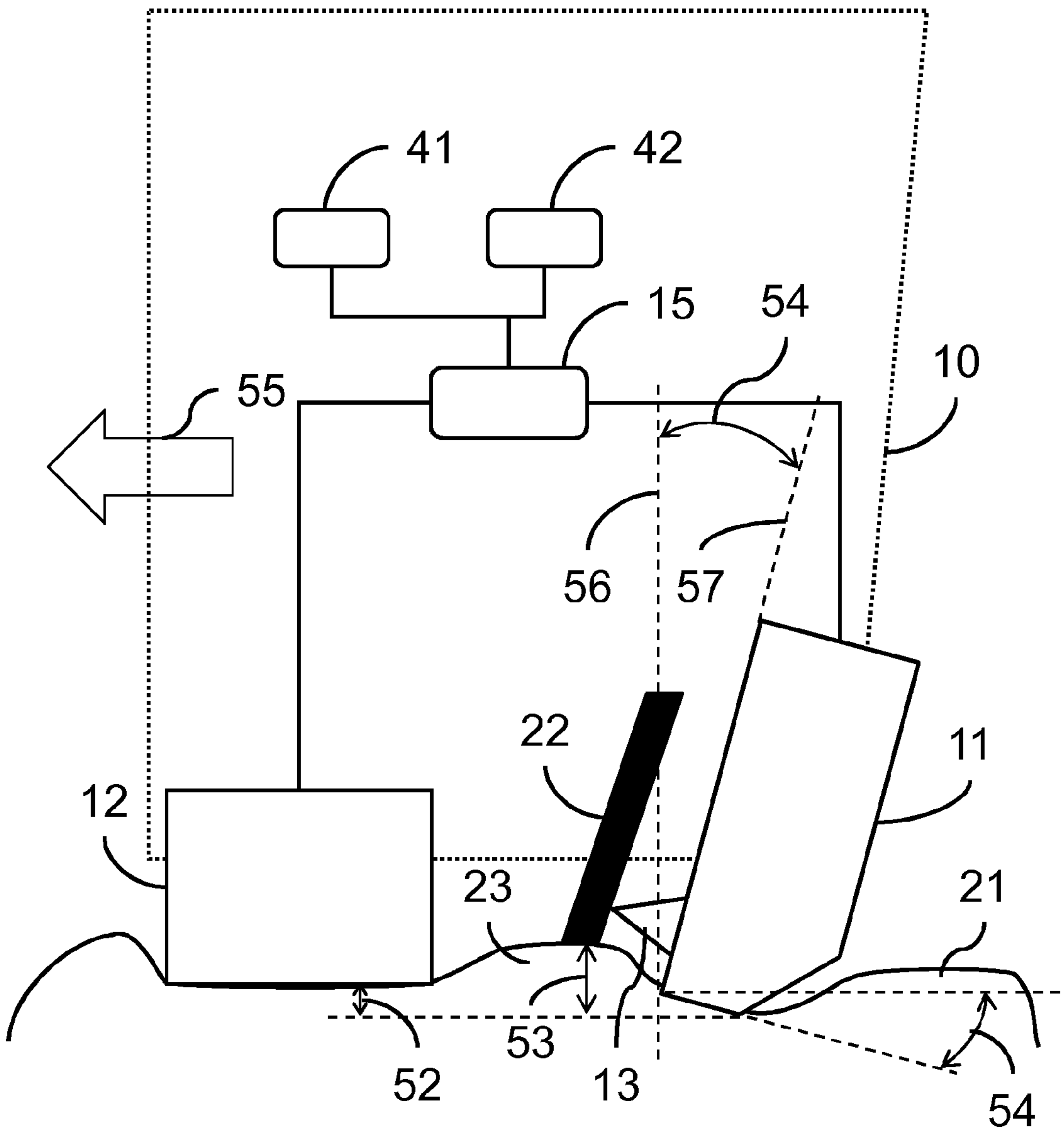
FIG. 3 shows the cross section of FIG. 1, with the cutter unit in a tilted position.

FIG. 2 schematically shows a top view cross section of the hair cutting device 10 of FIG. 1. FIG. 3 shows the cross section of FIG. 1, with the cutter unit 11 in a tilted position. In addition to adapting the slit size 51 and the exposure 52, also the cutter angle 54 between a neutral position 56 and a current position 57 of the front surface of the cutter unit 11 may be adapted. This cutter angle 54 is the same as the angle 54 between the skin-contact surface and the shaving direction 55. Changing the cutter angle 54 has two effects on the shaving process. A first effect is that the inclined skin-contact surface exerts a different pressure on the skin surface 21 than a flat skin-contact surface would do which may lead to a different dome shape and dome height 53. A second effect is that, because the light source is rotated together with the cutter unit 11, the focus of the hair cutting laser 13 will move away from or towards the skin surface 21. Both the change of the dome shape and the displacement of the focus of the hair cutting laser beam 13 affect the closeness and the irritation. For optimum skin dome control, the rotation angle of the cutter unit is preferably selected somewhere in the range of −15° to +15°.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb “comprise” and its conjugations does not exclude the presence of elements or steps other than those stated in a claim. The article “a” or “an” preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A hair cutting device comprising:

a cutter unit comprising a skin-contact surface for dragging over a skin surface in a shaving direction, a front surface arranged in front of the skin-contact surface in the shaving direction, and a laser beam exit window arranged in the front surface for allowing a hair cutting laser beam to cut a hair near the skin surface in front of the front surface, a skin stretcher being positioned in front of the cutter unit, according to the shaving direction, and comprising a stretcher surface for dragging over the skin surface together with the skin-contact surface, such that a skin dome is formed by the skin surface in a slit between the skin stretcher and the cutter unit, and slit adapting means for adapting at least one dimension of the slit for controlling a shape of the skin dome.

2. A hair cutting device as claimed in claim 1, wherein the slit adapting means comprise means for adapting a slit size, the slit size being a distance between a rear surface of the skin stretcher and the front surface of the cutter unit, measured in the shaving direction.

3. A hair cutting device as claimed in claim 1, wherein the slit adapting means comprise means for adapting an exposure, the exposure being a distance between the skin-contact surface and the stretcher surface measured in a direction perpendicular to the shaving direction.

4. A hair cutting device as claimed in claim 1, wherein the slit adapting means comprise means for adapting an angle between the skin-contact surface and the shaving direction.

5. A hair cutting device as claimed in claim 1, wherein the slit adapting means comprise at least one actuator for moving the cutter unit and/or the stretching element relative to a housing of the hair cutting device.

6. A hair cutting device according to claim 1, further comprising:

a light based hair detector for detecting the hair near the skin surface, a hair cutting laser source for generating the hair cutting laser beam, and a processor coupled to the light based hair detector and to the hair cutting laser source and being arranged to activate the hair cutting laser source in a focal position of the hair cutting laser beam in which the light based hair detector has detected the presence of the hair.

7. A hair cutting device as claimed in claim 6, wherein the processor is further coupled to the slit adapting means for controlling the slit adapting means.

8. A hair cutting device as claimed in claim 7, wherein the light based hair detector is further adapted to detect a height of the skin dome and wherein the processor is further arranged to control the slit adapting means in dependence of the detected height of the skin dome.

9. A hair cutting device as claimed in claim 8, wherein the light based hair detector employs a hair detecting laser beam for detecting the hair and/or the skin surface and wherein the height of the skin dome is detected by determining whether the skin dome is present at at least one selected height of the hair detecting laser beam in the slit.

10. A hair cutting device as claimed in claim 7, wherein the skin stretcher comprises a pressure sensor for determining a pressure exerted on the stretcher surface and wherein the processor is further arranged to control the slit adapting means in dependence of the determined pressure.

11. A hair cutting device as claimed in claim 7, wherein the skin stretcher comprises a friction sensor for determining a friction between the stretcher surface and the skin surface and wherein the processor is further arranged to control the slit adapting means in dependence of the determined friction.

12. A hair cutting device as claimed in claim 7, further comprising means for determining a speed of the hair treatment device relative to the skin surface and wherein the processor is further arranged to control the slit adapting means in dependence of the determined speed.

13. A hair cutting device as claimed in claim 1, wherein the cutter unit comprises an optical blade with a transparent blade body including the front surface and the laser beam exit window, wherein the blade body is adapted for guiding the hair cutting laser beam to the exit window.

* * * * *